United States Patent
Anderson et al.

(10) Patent No.: US 7,347,857 B2
(45) Date of Patent: Mar. 25, 2008

(54) ABLATION CATHETER HAVING A LOOP STRUCTURE FOR EFFECTING ABLATION OF TISSUE

(75) Inventors: Neil L. Anderson, Roseville (AU); Evan Chong, Roseville (AU)

(73) Assignee: CathRx Ltd., Eveleigh (AU)

( * ) Notice: Subject to any disclaimer, the term of this patent is extended or adjusted under 35 U.S.C. 154(b) by 0 days.

(21) Appl. No.: 10/514,308

(22) PCT Filed: May 9, 2003

(86) PCT No.: PCT/AU03/00559

§ 371 (c)(1),
(2), (4) Date: Nov. 9, 2005

(87) PCT Pub. No.: WO03/094764

PCT Pub. Date: Nov. 20, 2003

(65) Prior Publication Data

US 2006/0089634 A1  Apr. 27, 2006

(30) Foreign Application Priority Data

May 13, 2002  (AU) .................................... PS2264

(51) Int. Cl.
*A61B 18/18* (2006.01)

(52) U.S. Cl. .............................. 606/41; 606/45; 606/49

(58) Field of Classification Search .................. 606/41, 606/45, 49
See application file for complete search history.

(56) References Cited

U.S. PATENT DOCUMENTS 4,101,984  A    7/1978  MacGregor (Continued)

FOREIGN PATENT DOCUMENTS

EP    0 479 435 A2    4/1992

(Continued)

OTHER PUBLICATIONS

International Search Report mailed on Jul. 1, 2003, for PCT patent aplicationn No. PCT/AU03/00559 filed May 9, 2003, 6 pages.

(Continued)

*Primary Examiner*—Linda C. M. Dvorak
*Assistant Examiner*—Jacqueline Papapietro
(74) *Attorney, Agent, or Firm*—Morrison & Foerster LLP

(57) ABSTRACT

An ablation catheter (10) includes an elongate carrier (12). A first loop (14.1) is arranged at or adjacent a distal end of the carrier (12). At least one sensing electrode (40) is carried on the first loop (14.1) for sensing irregular activity in a patient's body. At least one further loop (14.2) is arranged proximally relative to the first loop (14.1) on the carrier (12) in a fixed orientation relative to the first loop (14.1). At least one ablating electrode (42) is carried on the second loop (14.2) for ablating a site of the patient's body where irregular electrical activity occurs. In another form of the invention, the ablation catheter includes a carrier (12) having a loop (14) defined at the distal end, the loop (14) comprising a first arm (18) and a second arm (22), the arms (18, 22) of the loop (14) being at least partly electrically isolated with respect to each other and at least one electrode (16, 20) arranged on each arm (18, 22) of the loop (14). In either form of the invention, an ablating electrode (42) carried on an outer periphery of the carrier (12) may be arranged only partially about the periphery of the carrier (12).

12 Claims, 2 Drawing Sheets

U.S. PATENT DOCUMENTS

| | | |
|---|---|---|
| 5,269,810 A | 12/1993 | Hull et al. |
| 5,522,874 A | 6/1996 | Gates |
| 5,722,401 A | 3/1998 | Pietroski et al. |
| 5,834,051 A | 11/1998 | Woloszko et al. |
| 5,931,862 A | 8/1999 | Carson |
| 6,071,278 A | 6/2000 | Panescu et al. |
| 6,106,522 A | 8/2000 | Fleischman et al. |
| 6,120,496 A | 9/2000 | Whayne et al. |
| 6,972,016 B2 * | 12/2005 | Hill et al. ............ 606/41 |
| 7,178,234 B2 | 2/2007 | Kawasaki et al. |
| 2001/0007070 A1 | 7/2001 | Stewart et al. |
| 2003/0093072 A1 * | 5/2003 | Friedman ............ 606/41 |

FOREIGN PATENT DOCUMENTS

| | | |
|---|---|---|
| EP | 0 479 435 A3 | 4/1992 |
| WO | WO-90/08466 A1 | 8/1990 |
| WO | WO-96/36860 A2 | 11/1996 |
| WO | WO-96/36860 A3 | 11/1996 |

OTHER PUBLICATIONS

Supplementary Partial European Search Report mailed Feb. 12, 2007 for EP Application No. 01977995.8, five pages.

* cited by examiner

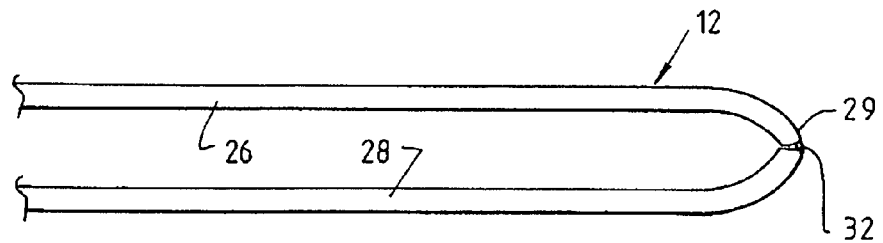
FIG. 1
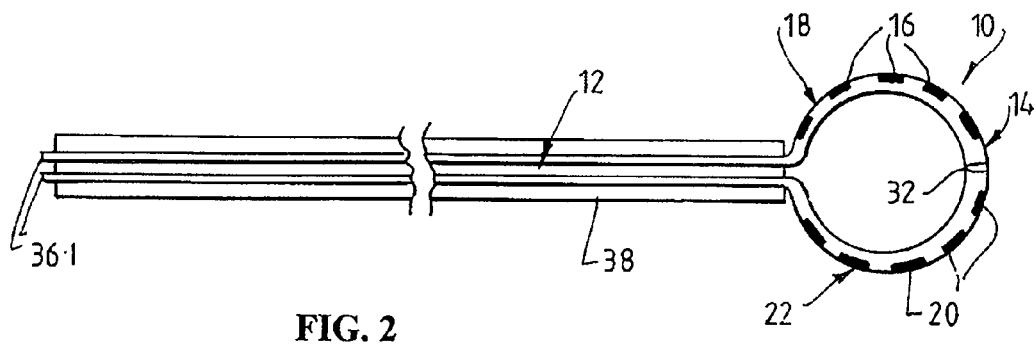
FIG. 2
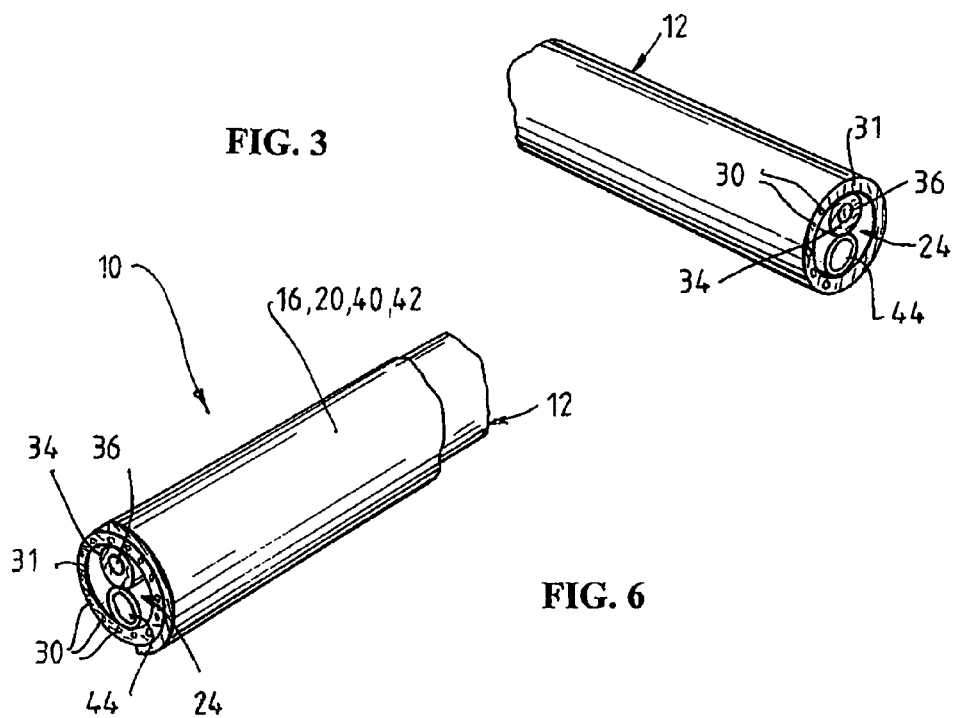
FIG. 3
FIG. 6

ABLATION CATHETER HAVING A LOOP STRUCTURE FOR EFFECTING ABLATION OF TISSUE

FIELD OF THE INVENTION

This invention relates to a catheter. The invention relates particularly, but not necessarily exclusively, to an ablation catheter for the treatment of atrial fibrillation.

BACKGROUND TO THE INVENTION

Atrial fibrillation is a condition that affects large groups of people with new patients being diagnosed each year. These patients have a lower quality of life as well as having up to a seven times increase in the likelihood of heart attacks or strokes. Current therapies include drug treatment or defibrillation, both palliative forms of treatment. Over the past few years, a number of research groups have been investigating curative treatment involving ablative techniques using radio frequency (RF), ultrasound, laser or microwave energy or cryoablation techniques.

Ablation therapy, while being promising, requires complex catheter designs. Such catheters also have to be reasonably thin to be manoeuvred through a patient's vascular system.

A current approach is the use of a catheter in the shape of a lasso which has a number of electrodes used for diagnostic purposes only. The lasso is positioned through the left atrium of the heart in pulmonary veins. As the lasso is round in shape, it surrounds the inside of the vein. Different sizes of catheters are required depending on the size and shape of the ostium. A typical procedure uses a first catheter to sense regions of irregular electrical activity and a second, separate, ablation catheter to ablate the specific site of irregular electrical activity. The procedure is repeated at various sites until all sites of irregular electrical activity have been blocked. One of the disadvantages associated with this procedure is the difficulty in guiding the ablation catheter to the exact site of the vein at which ablation is to occur. In this regard, it must be borne in mind that the first catheter which is used to sense the irregular electrical activity needs to be retained in position while the second catheter is inserted through the patient's vascular system to the site to guide the ablation catheter to that site. In addition, too much energy can lead to excessive tissue damage which can lead to stenosis of the blood vessel. Conversely, too little energy or insufficient ablated sites can lead to a reoccurrence of the irregular, electrically conductive pathways and therefore the likelihood of further atrial arrhythmia.

SUMMARY OF THE INVENTION

According to a first aspect of the invention, there is provided an ablation catheter which includes:
an elongate carrier;
a first loop arranged at, or adjacent, a distal end of the carrier;
at least one sensing electrode carried on the first loop for sensing irregular electrical activity in a patient's body;
at least one further loop arranged proximally relative to the first loop on the carrier in a fixed orientation relative to the first loop; and
at least one ablating electrode carried on the second loop for ablating a site of the patient's body where irregular electrical activity occurs.

Preferably, the catheter includes a plurality of sensing electrodes arranged at circumferentially spaced intervals about the first loop and a plurality of ablating electrodes arranged at circumferentially spaced intervals about the second loop. When viewed longitudinally along the carrier, each ablating electrode of the second loop may be aligned with a sensing electrode of the first loop.

The elongate carrier may include a tubular member defining a lumen and a shape forming member carried in the lumen for forming the loops. The shape forming member may be of a shape memory alloy such as a nickel, titanium alloy.

The tubular member may act as a mandrel for electrical conductors for the electrodes of the first loop and the second loop, the conductors being arranged about an outer surface of the tubular member and being covered with a coating of an insulating material. This leaves a lumen of the tubular member free for the passage of other elements, such as steering cables, conduits for cooling fluids etc. At predetermined locations along the coating, the coating may be removed to expose the conductors and electrodes may be applied at these exposed locations.

The tubular member may be folded back on itself to form a distal hairpin and a pair of limbs extending from the hairpin, the limbs having a pair of proximal ends, the loops being carried on the limbs and a size of each loop being adjustable by appropriate manipulation of the proximal end of at least one of the limbs.

An electrically isolating discontinuity may be arranged between the loops isolating the conductors of the first loop from the conductors of the second loop. The second loop may be arranged on one of the limbs proximally of the discontinuity with the first loop also being arranged on the first limb but between the discontinuity and the hairpin, the electrical conductors for the ablating electrodes of the second loop extending along the one limb and the electrical conductors for the sensing electrodes of the first loop extending along the other limb and through the hairpin into the one limb.

It will be appreciated that, because the lumen is free of conductors, it can be made more narrow. Also, the fact that conductors for each of the loops run in separate limbs of the tubular member means that more electrodes can be carried on each loop without adversely affecting the size of the catheter. As a result, the accuracy of sensing measurements and ablating procedures is improved because greater resolution is possible than has heretofore been the case.

In the manufacture of the catheter, the conductors may be mounted on the tubular member prior to folding the tubular member. The electrodes may be formed at the desired locations along the length of the conductors where after the tubular member is folded back on itself and cut to isolate the electrodes on one loop from the electrodes on the other loop with each set of electrodes having its own conductors. The shape forming member may then be inserted into the lumen of the tubular member to form the loops.

The first loop, which is arranged at a distal end of the catheter may have only electrodes without any temperature sensing means and may be used for sensing electrical activity in the pulmonary vein. The second loop, being proximally arranged relative to the first loop may, in use, be located at, or adjacent, the ostium of the pulmonary vein and may be used for ablating purposes. Thus, the second loop may include the electrodes and the temperature sensing means. It will be appreciated that the catheter may comprise more than two loops, with one being used for sensing and two being used for ablation or vice versa.

The electrodes of the second loop of the catheter may be used both for sensing undesirable or irregular electrical activity at, or adjacent, the ostium of the pulmonary vein and for ablating tissue at, or adjacent, the ostium of the pulmonary vein at where such undesirable electrical activity occurs. Thus, where any electrode of the first loop or the second loop senses undesirable electrical activity, the relevant electrode or electrodes of the second loop may be used to ablate the tissue to form a lesion in the region of the ostium to disrupt the electrically conductive pathway in the tissue to reduce atrial fibrillation.

The catheter may include a tubular introducer for introducing the carrier into the patient's body, the carrier being slideably received in a passage of the introducer and being slideable relative to the introducer between a first, retracted position in which the loops are contained in a collapsed configuration in the passage of the introducer and a second, extended configuration in which the loops are in an expanded, loop-shaped configuration and are distally arranged relative to a distal end of the introducer. When the loops are in their second, extended configuration, each loop may lie in a plane transverse to a longitudinally axis of the carrier. The planes may be substantially parallel to each other.

As a result of the looped arrangement of the electrodes, when the catheter is inserted into the blood vessel, an operator will know which parts of each loop and, hence, which side of each electrode is in contact with a wall of the blood vessel and which side is in contact with blood within the blood vessel. As it is undesirable to impart heat to the blood carried in the blood vessel, each electrode may be cuff-shaped to extend only partway about the periphery of the carrier, the arrangement being such that the electrodes are arranged on an outer side of their loops. By "cuff-shaped", it is meant that the electrodes are semi-circular cylindrical in shape.

Each of at least certain of the electrodes at least on the second loop may have a temperature measuring facility associated with it. The temperature measuring facility may be a thermocouple. Those electrodes operative also to measure temperature may therefore have three conductors associated with them. Those electrodes used only for sensing or ablating may only have a single conductor associated with them.

According to a second aspect of the invention, there is provided an ablation catheter which includes an elongate carrier having a loop defined at a distal end, the loop comprising a first arm and a second arm, the arms of the loop being at least partly electrically isolated with respect to each other; and at least one electrode arranged on each arm of the loop.

Preferably, each arm carries a plurality of electrodes. The electrodes may be serially arranged along a length of each arm.

The carrier may comprise a tubular member defining a lumen with a shape forming member being received in the lumen for forming the loop.

The tubular member may act as a mandrel for electrical conductors for the at least one electrode of the loop, the conductors being arranged about an outer surface of the tubular member and being covered in a coating of an insulating material.

The tubular member may be folded back on itself to form a distal hairpin and a pair of limbs extending from the hairpin, each limb having proximal end, the arms of the loop being defined by distal portions of the limbs on opposite sides of the hairpin.

The arms of the loop may be electrically isolated from each other at a distal end of the loop. Thus, the tubular member may include an electrically isolating discontinuity at the distal end of the arms, more particularly, at the hairpin. For example, the arms may be cut and then re-connected in an electrically isolated manner.

By "at least partly electrically isolated, it is meant that, in respect of most conductors of each limb, the conductors terminate before, or at, the discontinuity. However, it may be required that at least certain of the conductors traverse the discontinuity, ie. extend up through one limb and return through the other limb. Such conductors would then not be terminated before, or at, the discontinuity.

A temperature measuring facility may be associated with at least certain of the electrodes.

The electrodes may be shaped only to be on an operatively outer part of the loop. More specifically, each electrode is substantially semi-cylindrical in shape, or cuff-shaped, as opposed to being in the form of a band or annulus.

The semi-cylindrical electrodes may be longer than band-shaped electrodes so that a surface area of each semi-cylindrical electrode is substantially the same as that of a conventional band-shaped, ablating electrode to have the same current density in the semi-cylindrical ablating electrodes, in use.

According to a third aspect of the invention, there is provided an ablation catheter which includes an elongate carrier defining an outer periphery; and at least one ablating electrode carried on said outer periphery, said at least one ablating electrode being arranged only partially about the periphery of the carrier.

The outer periphery may be a radially outer part of at least one loop carried by the carrier and the at least one electrode may be carried partially about the radially outer part of the at least one loop. The at least one electrode may be of semi-cylindrical shape.

In the case of all aspects as described above, a source of energy for effecting ablation may be selected from the group comprising radio frequency, microwave, ultrasound, laser and cryoablative energy.

BRIEF DESCRIPTION OF THE DRAWING

The invention is now described by way of example with reference to the accompanying drawings in which:-

FIG. 1 shows a schematic representation of an ablation catheter, in accordance with a first aspect of the invention, in an initial stage of formation;

FIG. 2 shows a schematic representation of the catheter;

FIG. 3 shows a schematic representation of an interior cross section of the catheter;

FIG. 6 shows a schematic, cross sectional view of an ablation catheter, in accordance with a third aspect of the invention.

DETAILED DESCRIPTION OF THE INVENTION

Figure 4:
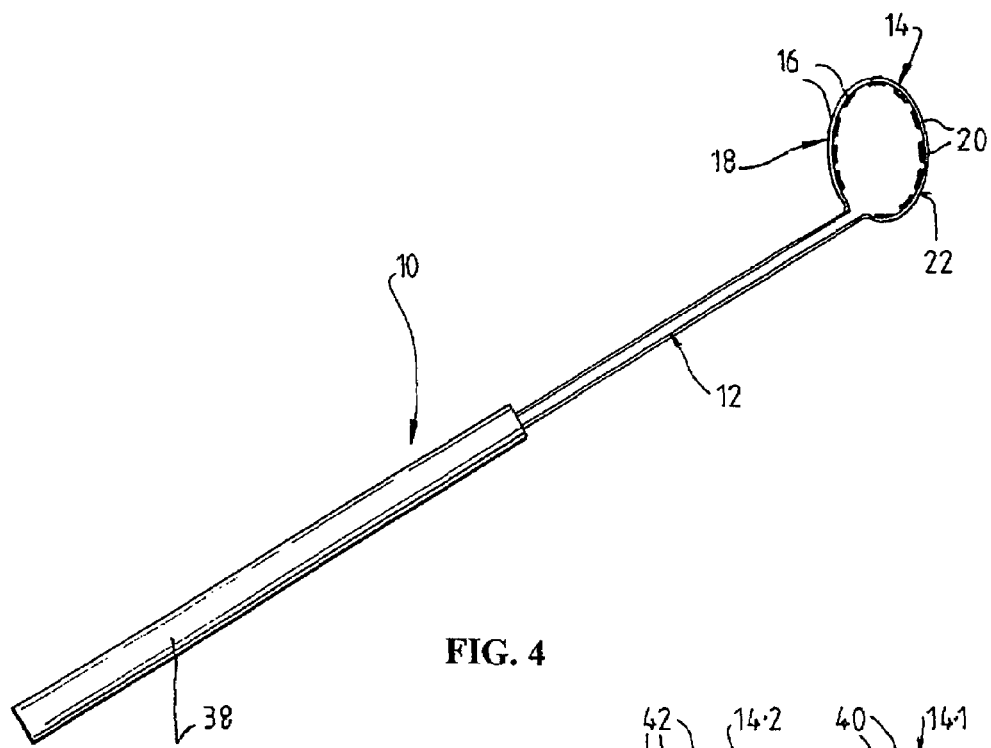
FIG. 4 shows a three dimensional view of an ablation catheter, in accordance with the first aspect of the invention.

In the drawings, reference numeral 10 generally designates an ablation catheter, in accordance with the invention. The catheter 10 includes an elongate carrier in the form of a tubular member 12 having a loop 14 defined at a distal end of the carrier 12, the loop 14 being formed by two arms 18, 22. The arms 18, 22 are joined at a distal end of the loop 14. A plurality of electrodes 16 is carried on one arm 18 of the loop 14 with a similar number of electrodes 20 being carried on the opposed arm 22 of the loop 14.

The tubular member 12 defines lumen 24.

In the fabrication of the catheter 10, in accordance with one embodiment of the invention and as shown in FIG. 1 of the drawings, the tubular member 12 is folded back on itself into a substantially hairpin shape to define a pair of limbs 26, 28 joined at a hairpin 29. Conductors, five of which are shown schematically at 30 in FIG. 3 of the drawings, are embedded in a wall of the tubular member 12. In the fabrication of the tubular member, once the conductors 30 have been placed in position about the outside part of the tubular member 12 defining the lumen 24, a covering or coating 31 of an insulating material is applied to the conductors 30 to form the finished tubular member 12.

At the distal end of the tubular member 12, the coating of insulating material 31 is removed to expose the conductors 30. Metal is applied by a deposition technique to form the electrodes 16, 20. The metal of the electrodes 16, 20 is of a bio-compatible material such as a noble metal, for example, platinum.

Once the electrodes 16, 20 have been formed, the tubular member 12 is cut at its distal end, as indicated at 32 in FIGS. 1 and 2 of the drawings. This includes cutting the conductors 30. The cut ends are re-joined in an electrically isolated manner to form the two arms 18, 22 of the loop 14.

As illustrated in FIG. 3 of the drawings, a further tube 34 is inserted into the lumen 24 of the tubular member 12. This tube 34 accommodates a shape forming member 36 such as a length of nickel, titanium alloy (Nitinol™) which is used in forming each arm 18, 22 of the loop 14, as will be described in greater detail below. The length of shape forming member 36 has two, protruding, proximal ends 36.1

The catheter 10 includes an introducer or sleeve 38 in which the hairpin shaped tubular member 12 is received for use The ends 36.1 of the shape forming member 36 protrude from a proximal end of the introducer 38 and are used for adjusting the size of the loop 14 to cater for various sizes of pulmonary vein ostia. The introducer 38 includes a steering mechanism (not shown) for steering the catheter 10 through the vascular system and heart of a patient undergoing treatment.

In use, to treat atrial fibrillation, the catheter 10 is inserted via the patient's vascular system and the left atrium of the heart into the ostium of the pulmonary vein to be treated where atrial arrhythmia may be occurring. To facilitate insertion of the catheter 10, the loop 14 is retracted into the introducer so that the loop 14 adopts a collapsed configuration within the introducer 38 as the introducer 38 is steered to the relevant site by an operator. At the desired location relative to the ostium, the tubular member 12 is urged towards the distal end of the introducer 38 to eject the loop-defining part of the tubular member 12 out of the distal end of the introducer 38, the length of shape forming member 36 acting on the distal end of the tubular member 12, as the distal end of the tubular member 12 escapes from the introducer 38, to form the arms 18, 22 of the loop 14.

Sensing of electrical activity at or adjacent the ostium takes place by the electrodes 16 and 20 acting as sensing electrodes.

To assist the clinician in placement of the loop 14 relative to the pulmonary vein, radio opaque tokens (not shown) in the form of bands may be arranged at various location on the loop 14. The radio opaque bands may be identified with certain of the electrodes 16, 20 so that the clinician knows exactly where the electrodes 16, 20 are positioned at the various locations about the wall of the pulmonary vein. This is only necessary if the electrodes 16, 20 are not visible under a fluoroscope.

An additional lumen 44 extends along the lumen 24 of the tubular member 12 to the electrodes 16, 20 to provide delivery of a fluid, such as a saline solution, to the electrodes 16, 20 during ablation. Due to the fact that the electrodes 16, 20 are coated on the tubular member 12, this facilitates the formation of an opening through each electrode 16, 20 through which the saline solution can be delivered. Instead of the saline solution being ejected through openings in the electrodes, the solution could, instead, be circulated through a suitable conduit (not shown) arranged in the lumen 24 of the tubular member 12 and extending through the limbs 26, 28 of the tubular member. In this way, the electrodes 16, 20 may be cooled allowing for higher energies and deeper lesions while inhibiting overheating of the tissue or blood in the vessel.

FIG. 4 of the drawings shows a configuration where a single loop 14 is provided. In this embodiment of the invention, the electrodes 16, 20 are used both for sensing of electrical activity as well as for ablating purposes.

Figure 5:
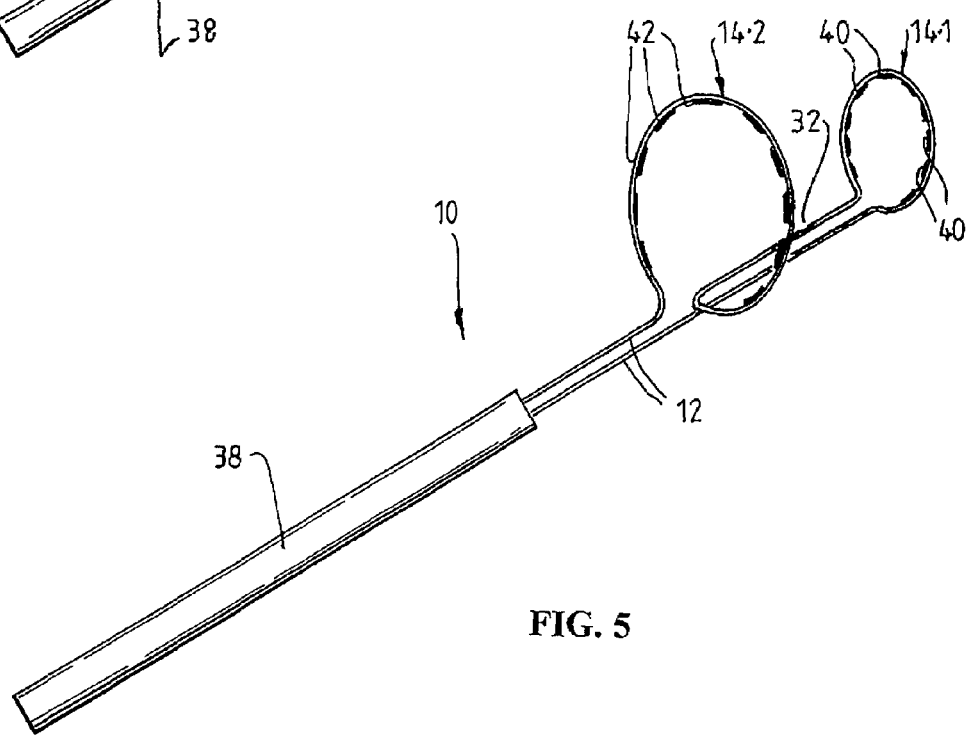
FIG. 5 shows a three dimensional view of an ablation catheter, in accordance with a second embodiment of the invention.

In the embodiment of the invention shown in FIG. 5 of the drawings, a catheter 10 is provided which includes two loops 14.1 and 14.2. The loop 14.1 is arranged at the distal end of the catheter 10 and includes only sensing electrodes 40 arranged about the loop 14.1.

The loop 14.2 is arranged proximally relative to the loop 14.1 and includes only ablating electrodes 42 arranged about the loop 14.2. However, if desired, the electrodes 42 of the loop 14.2 are also used for sensing of irregular electrical activity, in addition to performing their ablating function.

In the formation of the catheter 10 of FIG. 5, the cut 32 formed in the tubular member 12 is arranged proximally of the hairpin 29 so that the loop 14.2 is formed proximally of the cut 32 and the loop 14.1 is formed intermediate the cut 32 and the hairpin 29. The conductors 30 for the loop 14.2 extend along the limb 26 of the tubular member 12, the limb 26 terminating at the cut 32. The conductors 30 for the loop 14.1 extend along the limb 28 of the tubular member 12, the limb 28 forming the hairpin 29 and terminating at the cut 32. It is to be noted that, in this embodiment of the invention, it is not essential that the conductors 30 for each of the loops 14.1 and 14.2 extend along separate limbs. In other words, the cut 32 in the tubular member 12 is not essential.

In use, the catheter 10 of FIG. 5 is used in a similar manner to that described above with reference to FIG. 4. The catheter 10 is introduced into the patient's vascular system with the loops 14.1 and 14.2 retracted, in a collapsed configuration into the introducer 38. The catheter 10 is inserted via the left atrium of the patient's heart. At the relevant pulmonary vein, the loops 14.1 and 14.2 are urged distally out of the introducer 38 so that the shape forming member 36 causes the loops 14.1 and 14.2 to form. When the loops 14.1 and 14.2 are ejected from the catheter 10, they adopt an erected configuration in which the loops 14.1 and 14.2 lie in planes that are substantially parallel to each other and transversely to a longitudinal axis of the catheter 10. The loop 14.1 is received within the pulmonary vein with the loop 14.2 being arranged at, or adjacent, the ostium. The electrodes 40 and 42 are arranged on the loops 14.1 and 14.2, respectively, so that they are aligned with each other longitudinally along the tubular member 12. The spacing between the loops 14.1 and 14.2 is such that, in all likelihood, should adverse electrical activity be picked up by one of the electrodes 40 of the loop 14.1, the corresponding, aligned electrode 42 of the loop 14.2 can be used to ablate the tissue at the ostium which should result in ceasing of the adverse electrical activity. Accordingly, this aspect of the invention provides separate electrodes for sensing and for ablating purposes.

Referring now to FIG. 6 of the drawings, a part of the catheter 10 showing one of the electrodes 16, 20, 40 or 42, in accordance with another aspect of the invention, is illustrated. The electrodes 16, 20, 40 or 42 do not extend all the way about the periphery of the tubular member 12. Rather, the electrodes 16, 20, 40 or 42 are each in the form of a cuff-like member which extends only part way, approximately halfway, about the periphery of the tubular member 12. Hence, when the loop or loops 14 are formed, the cuff-like electrode 16, 20, 40 or 42 as the case, are arranged on a part of each loop facing radially outwardly to be in contact with the wall of the pulmonary vein to effect sensing/ablating. With this configuration of electrodes 16, 20, 40, 42 electrical energy is focused towards ablating the tissue rather than ablating and coagulating blood in the vessel. This improves the creation of the lesion in the wall of the vein and optimises the size/depth of the lesion while lessening the likelihood of stenosis of the vein occurring.

A further benefit of this arrangement is that, with comparison to a band-type electrode, the cuff-type electrode 16, 20, 40 or 42 has a greater length to provide a similar surface area to the band-type electrode. The greater length of the cuff-shaped electrode 16, 20, 40 or 42 means that a longer lesion can be formed with the same current density as presently used.

Further, as illustrated in FIGS. 3 and 6 of the drawings, because the conductors 30 for the electrodes 16, 20, 40, 42 are embedded in a wall of the tubular member 12, it results in a catheter 10 which is thinner than multi-electrode catheters of the type presently in use. This facilitates manipulation of the catheter 10 through the vessels and/or heart of the patient. It also means that the lumen 24 of the tubular member 12 is free to accommodate the length of shape-forming member 36 and, where applicable, the conduit 44 for the delivery of a saline solution.

While the catheter 10 has been described with reference to its application in the treatment of atrial fibrillation, it will be appreciated that the catheter 10 could also be used in other applications such as in the treatment of ventricular tachycardia. It could also be used in non-cardiac applications such as in the ablation of tumours or of the prostate.

Further, it is to be noted that any electrode that is being used of ablation can have a thermocouple pair underneath it if needed. Thus some of the ablating electrodes have three conductors 30 associated with them while others only have one conductor 30. Separate electrodes to be used as thermocouples could also be provided but this would increase the number of electrodes. Such separate electrodes would each have two conductors 30 associated with them.

An example of a catheter 10 is given below:

A one metre length of 0.4 mm stiff shape forming wire 36 which has two loops 14.1 and 14.2, each of 20 mm diameter shape formed therein and positioned halfway along the length of the wire 36 was passed in a lumen 24 of a tubular member 12 of 1.6 mm diameter with a Pebax™ jacket 31. The tubular member 12 carried twenty 0.16 mm conductors 30 helically wound around an outer surface of the lumen 24 and embedded in the jacket 31. The tubular member 12 was folded back on itself so that the loops 14.1 and 14.2 were arranged at the distal end with the loop 14.2 being arranged proximally of the loop 14.1. The folded tubular member 12 had the ends 36.1 of the shape forming wire 36 protruded from the aligned proximal ends of the tubular member 12 and was inserted in an introducer 38 so that the loops 14.1 and 14.2 could be ejected through a distal end of the introducer 38 to adopt their erected configuration. It was shown that, by manipulating the ends 36.1 of each limb 26, 28 of the tubular member 12 relative to the introducer 38, the diameter of each of the loops 14.1 and 14.2 could be adjusted independently of each other.

It is a particular advantage of the invention that a catheter 10 is provided which is used both for sensing and ablating in the treatment of atrial fibrillation. Also, with the construction of the tubular member 12 having the conductors 30 embedded therein, a catheter 10 which is of thinner construction than catheters of which the applicant is presently aware, can be formed resulting in easier manipulation of the catheter 10.

Another advantage of the catheter 10 of the present invention is that, in comparison with existing catheters, the split construction of the tubular member 12 means that double the number of conductors 30 can be accommodated and, consequently, double the number of electrodes 16, 20, 40 or 42. This has the benefit that more electrodes can be carried on each loop 14 without adversely affecting the size of the catheter 10. As a result, the accuracy of sensing measurements and ablating procedures is improved because greater resolution is possible than has heretofore been the case.

With the double loop configuration of the catheter 10, the fact that the loops 14.1 and 14.2 are in a fixed orientation relative to each other reduces the risk of the loop 14.1 being inserted too deeply into the pulmonary vein. As a result the likelihood of trauma to the vein is reduced.

Prior art catheters of which the Applicant is aware perform a circumferential ablation. Still another advantage of the present invention is that individual electrodes can be controlled independently to ablate small, segmented regions of tissue rather than creating an entire circular lesion. As a result, less trauma is caused to the patient and more accurate directing of the ablating at the target site can be effected.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An ablation catheter which includes:
   an elongate carrier which is folded back on itself to form a distal hairpin and a pair of limbs extending from the hairpin;
   a first loop arranged at, or adjacent, a distal end of the carrier;
   at least one sensing electrode carried on the first loop for sensing irregular electrical activity in a patient's body;
   at least one further loop arranged proximally of the first loop on the carrier in a fixed orientation relative to the first loop; and
   at least one ablating electrode carried on the at least one further loop for ablating a site of the patient's body where irregular electrical activity occurs; and
   an electrically isolating discontinuity arranged on a first limb of the pair of limbs of the carrier and between the loops to isolate electrical conductors associated with the first loop from electrical conductors associated with the at least one further loop, the at least one further loop being arranged on the first limb but between the discontinuity and the hairpin, the electrical conductors for the at least one ablating electrode of the at least one further loop extending along the first limb and the electrical conductors for the at least one sensing electrode of the first loop extending along a second limb of the pair of limbs and through the hairpin into the first limb.

2. The catheter of claim 1 which includes a plurality of sensing electrodes arranged at circumferentially spaced intervals about the first loop and a plurality of ablating electrodes arranged at circumferentially spaced intervals about the at least one further loop.

3. The catheter of claim 2 in which, when viewed longitudinally along the carrier, each ablating electrode of the at least one further loop is a aligned with a sensing electrode of the first loop.

4. The catheter of claim 1 in which the elongate carrier includes a tubular member defining a lumen and a shape forming member carried in the lumen for forming the loops.

5. The catheter of claim 4 in which the conductors are arranged about a part of the tubular member defining the lumen and the conductors being covered with a coating of an insulating material so that the conductors are embedded in a wall of the tubular member.

6. The catheter of claim 1 in which each limb has a proximal end with a size of each loop being adjustable by manipulation of the proximal end of at least one of the limbs.

7. The catheter of claim 2 in which the ablating electrodes also perform a sensing function.

8. The catheter of claim 1 which includes a tubular introducer for introducing the carrier into the patient's body, the carrier being slideably receivable in a passage of the introducer and being slideable relative to the introducer between a first, retracted position in which the loops are contained in a collapsed configuration in the passage of the introducer and a second, extended configuration in which the loops are in an expanded, loop-shaped configuration and are distally arranged relative to a distal end of the introducer.

9. The catheter of claim 8 in which, when the loops are in their second, extended configuration, each loop lies in a plane transverse to a longitudinal axis of the carrier.

10. The catheter of claim 2 in which each electrode is cuff-shaped to extend only partway about the periphery of the tubular member, the arrangement being such that the each electrode is arranged on an outer side of its associated loop.

11. The catheter of claim 2 in which each of at least some of the electrodes of the at least one further loop have a temperature measuring facility associated with it.

12. The catheter of claim 1 further comprising a source of energy for effecting ablation wherein the energy is selected from the group consisting of radio frequency, microwave, ultrasound, laser and cryoablative energy.

* * * * *